(12) United States Patent
Castro (10) Patent No.: US 7,372,063 B2
(45) Date of Patent: May 13, 2008

(54) OPTICAL DETECTOR FOR THE PRESENCE OF GAS BUBBLES IN A LIQUID

(75) Inventor: Pascal Castro, Ouistreham (FR)

(73) Assignee: SC2N Societe Anonyme, Creteil (FR)

(*) Notice: Subject to any disclaimer, the term of this patent is extended or adjusted under 35 U.S.C. 154(b) by 0 days.

(21) Appl. No.: 10/536,472

(22) PCT Filed: Nov. 25, 2003

(86) PCT No.: PCT/FR03/03480

§ 371 (c)(1),
(2), (4) Date: May 25, 2005

(87) PCT Pub. No.: WO2004/051211

PCT Pub. Date: Jun. 17, 2004

(65) Prior Publication Data

US 2006/0061763 A1    Mar. 23, 2006

(30) Foreign Application Priority Data

Nov. 26, 2002   (FR) ................................. 02 14805

(51) Int. Cl.
*G01N 15/06* (2006.01)
*G01N 21/00* (2006.01)

(52) U.S. Cl. .................. 250/573; 250/574; 356/441
(58) Field of Classification Search ............ 250/573, 250/574; 356/441, 442
See application file for complete search history.

(56) References Cited

U.S. PATENT DOCUMENTS

| | | | | |
|---|---|---|---|---|
| 4,659,218 A | * | 4/1987 | de Lasa et al. | 356/133 |
| 4,740,709 A | * | 4/1988 | Leighton et al. | 250/573 |
| 4,749,871 A | * | 6/1988 | Galvin et al. | 250/573 |
| 4,885,676 A | * | 12/1989 | Zweighaft | 700/73 |
| 4,902,137 A | * | 2/1990 | Krieg et al. | 356/427 |
| 5,508,521 A | * | 4/1996 | Kraft et al. | 250/574 |
| 6,315,955 B1 | * | 11/2001 | Klein | 422/73 |

FOREIGN PATENT DOCUMENTS

WO    WO 98/55849    * 12/1998

* cited by examiner

*Primary Examiner*—Thanh X. Luu
*Assistant Examiner*—Brian J Livedalen
(74) *Attorney, Agent, or Firm*—Osha Liang LLP (57) ABSTRACT

The invention concerns a method for detecting gas bubbles in a liquid adapted to a device comprising a light source, a light detector and a data controlling and processing unit connected to a client system comprising the following steps: emitting light from the light source, acquiring successive measurements of the light intensity sensed by the light detector and calculating a variation between two successive measurements of said light intensity. In accordance with a first embodiment of the invention, the method further comprises a step which consists in comparing the variation between two successive measurements of light intensity to a threshold S. Advantageously, a warning counter is incremented by a value A when variation between two successive measurements is higher than the threshold S and decremented by a value B in the opposite case. A proportion of bubbles higher than a maximum authorized rate is detected when said warning counter exceeds a warning value C. In a second embodiment of the invention, the method further comprises a step which consists in calculating an average value between the variations between two successive measurements of light intensity. The client system is made aware of said average value proportional to said bubble content in the liquid.

22 Claims, 5 Drawing Sheets

OPTICAL DETECTOR FOR THE PRESENCE OF GAS BUBBLES IN A LIQUID

The invention concerns the domain of optical detectors for the presence of gas bubbles in a liquid.

The invention can be utilised non-exclusively for detection of gas bubbles in a water circuit for cooling an internal combustion engine of a motor vehicle.

It is well known to detect the presence of gas bubbles present for example in a cooling system by means of a light source, a light detector and a conversion device producing a signal in response to the quantity of light originating from the light source and received by the detector.

The document WO 98/55849 describes a device for detecting a gas leak in a cooling system by utilising means for detection of the presence of gas bubbles.

The device used in the document WO 98/55849 comprises a light source aligned with a light detector such that the source and the detector are optically coupled via an optical path, the latter being defined by the trajectory borrowed by the light between its emission by the source and its reception by the detector. A conversion device, connected to the light detector, produces an electronic signal in response to the quantity of light received by the light detector and originating from the light source.

This device compares the electronic signal in response to the quantity of light received by the light detector to a reference signal corresponding to the quantity of light received by the detector when the optical path is not obstructed by the passage of a bubble. If this difference is superior to a predetermined threshold value, then the passage of a gas bubble across the optical path is detected. This device makes it possible to detect the presence of gas bubbles in the cooling system, a sign of the presence of a leak in said cooling system.

This mode of comparison to a reference value does however have a number of drawbacks.

First of all, it consists of a mode of detection such that the response time to the presence of bubbles is uniform. The presence of a significant quantity of bubbles is thus detected just as rapidly as that of a small quantity. However, small quantities of bubbles are to be analysed more finely to ensure that detection is founded and to prevent an alarm from being triggered unnecessarily.

Moreover, the reference value is fixed in time. The system has optical deviations (soiling, opacification, etc.) and undergoes variations in temperature such that its properties are modified over the course of time. The sensitivity of the system is then altered and it is possible that after a certain time bubbles are not detected and that the corresponding alarm is therefore not triggered. It is likewise possible that a small quantity of bubbles is considered as being too important and that a false alarm is then triggered.

An aim of the invention is to propose an optical detection device for the presence of bubbles which is both simple, economical and reliable, while rectifying the drawbacks of the abovedescribed systems.

For this purpose, the invention proposes a process for detection of gas bubbles in a liquid adapted to a device comprising a light source, a light detector and a data controlling and processing unit linked to a client system comprising the steps of acquisition of successive measurements of light intensity originating from the light source and perceived by the light detector and calculation of the variation between two successive measurements of said light intensity.

The time span between two successive measurements is very short with respect to the time to be observed so that the sensitivity of the system is altered significantly due in particular to the optical deviations and the variations in temperature. As a result, the transformations of the properties of the system during said time span between two successive measurements cannot distort the measurement of the variation in light intensity between two successive measurements. The process according to the invention, is thus insensitive to time modifications of the properties of the system.

It is provided in a first preferred embodiment of the invention that the process of detecting gas bubbles in a liquid comprises, in addition, a comparison step of said variation between two successive measurements of light intensity to a predefined threshold value S. The system used in this preferred embodiment of the invention thus detects the presence of a gas bubble in the liquid if the measurement of the variation between two successive measurements of light intensity is greater than this threshold S.

It is advantageously provided within the scope of the first preferred embodiment of the invention that the data controlling and processing unit also comprises a warning counter incremented by a predefined value A when the variation between two successive measurements of light intensity perceived by the detector is greater than the threshold S and decremented by a predefined value B in the opposite case. The warning counter has, as an option, a predefined alarm value C, such that if the value of said warning counter exceeds the alarm value C, the client system is informed that the maximum authorised bubble content has been exceeded. The warning counter likewise has as an option a predefined value D, known as the final alarm value, such that the client system continues to be informed that the bubble content is greater than the maximum authorised bubble content and when the warning counter is lower than said final alarm value D. This embodiment rapidly makes it possible to detect a significant quantity of bubbles and detects a small quantity of bubbles longer and more precisely.

It is provided in a second preferred embodiment of the invention that the process for detection of gas bubbles also comprises a calculation step of the average value of a plurality of said variations between two successive measurements of light intensity. The system used in this second preferred embodiment of the invention then sends this average value which is representative of the gas bubble content in the liquid.

Advantageously, it is likewise provided that the data controlling and processing unit also comprises a control module for the light source capable of controlling the polarisation value of the light source, making it possible to carry out a new calibration of the system. This control module of the light source is especially capable of performing periodical polarisation of the light source. It can, as an option, have a detector for exceeding a predefined polarisation threshold. With such a threshold exceeding detector, it is possible, under certain conditions linked to the selected optical configuration, to detect whether the sensor constituted by the source and the light detector is immersed in the liquid or not.

Advantageously, the source and the light detector are arranged noticeably orthogonally. The step of acquisition of the successive measurements of light intensity perceived by the light detector then makes it possible to acquire measurements of the quantity of light rays emitted by the light source which are reflected should the occasion arise during the presence of bubbles on the surface of a bubble in a direction noticeably orthogonal to the direction of incidence towards the light detector.

The source and the light detector can likewise be arranged substantially adjacently. The step of acquiring the successive measurements of light intensity perceived by the light detector then makes it possible to acquire measurements of the quantity of light rays emitted by the light source which are reflected should the occasion arise during the presence of bubbles on the surface of a gas bubble in a direction noticeably parallel to the direction of incidence towards the light detector.

As an option, a temperature measuring element and at least one switch associated with said temperature measuring element can be added to the device. Advantageously, the switch is capable of changing state during the detection of a gas bubble.

The data controlling and processing unit transmits, via an interface module, to the client system the information on the temperature of the liquid and the presence of gas bubbles in the liquid. A high-amplitude level signal proportional to the temperature of the liquid when the presence of a bubble is not detected or low level when the presence of a bubble is detected is then provided to the client system on a single wire.

As an option, a system of electrodes capable of measuring the resistivity of the ambient conditions can likewise be added to the device. The client system is then informed that the sensor constituted by the source and the light detector is not immersed in the liquid when the electrode system identifies the ambient conditions as not being liquid. The switch associated with the temperature element then advantageously changes state during detection of a gas bubble and during the absence of liquid. The client system can then be informed by a high-amplitude level signal proportional to the temperature of the liquid when the presence of a bubble is not detected and when the sensor is immersed in the liquid, or low level when the presence of a bubble is detected or when the sensor is not immersed in the liquid.

Advantageously, the source and the light detector are arranged noticeably face to face. The step of emitting the light then makes it possible to emit from the light source a specific long-wave light such that it is strongly (reciprocally weakly) absorbed by the liquid and weakly (reciprocally strongly) absorbed by the gas constituting the bubbles. Optionally, the acquisition step of successive measurements of light intensity perceived by the light detector can make it possible to acquire measurements of the quantity of light rays emitted by the light source which are deviated towards the light detector should the case arise during the presence of bubbles due to the differences in diffraction index between the liquid and the gas constituting the bubbles on the level of the surface of said bubbles.

As an option, a temperature measuring element and at least one switch linked to said temperature measuring element can be added to the device. Advantageously, the switch changes state during the detection of a gas bubble.

The data controlling and processing unit transmits, via an interface module, to the client system the information on the temperature of the liquid and the presence of bubbles in the liquid. A periodic signal is supplied to the client system on a single wire and the period of said signal is formed from a first phase constituted by a constant level signal of high amplitude proportional to the temperature of the liquid and from a second phase constituted by a train of impulses of modulated width, the width of the impulses being modulated according to the average value of the successive variations in light intensity perceived by the light detector.

Advantageously, the client system can be informed that the sensor is not immersed in liquid when the polarisation value of the light source exceeds a predefined threshold value T, known as the polarisation alarm threshold value.

The client system can then be informed of information on the temperature of the liquid, the presence of bubbles in the liquid and the non immersion of the sensor in the liquid by a periodic signal wherein the period is formed by a first phase constituted by a constant level signal of high amplitude proportional to the temperature of the liquid and by a second phase constituted by a train of impulses of modulated width, the width of the impulses being modulated according to the average value of the successive variations in light intensity perceived by the light detector and said width being maximum when the sensor is not immersed in the liquid.

The invention likewise concerns a device for detecting gas bubbles in a liquid comprising light emission means, light detection means and data controlling and processing means linked to the light detection means, characterised in that following the emission of light by the light emission means and detection of light by the light detection means, the data controlling and processing means are capable of obtaining light detection means of the successive measurements of light intensity detected by the light detection means and of calculating a variation in light intensity between two successive measurements of light intensity.

Other characteristics, aims and advantages of the invention will emerge from reading the detailed description which will follow, and with reference to the appended figures, given by way of non-limiting examples and wherein.

Figure 1:
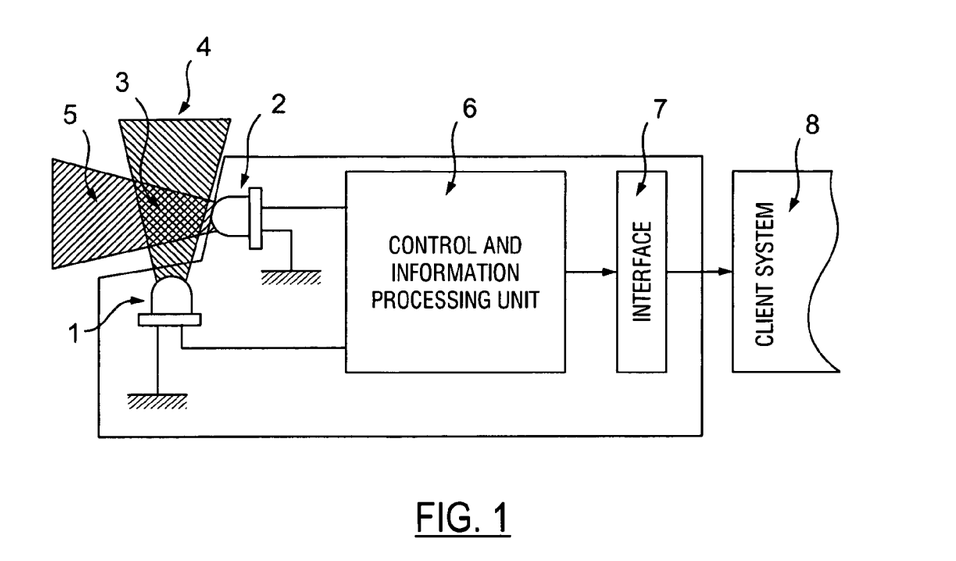
FIG. 1 illustrates a synoptic of the device for detecting gas bubbles in a liquid according to a first arrangement of the light source and the light detector.
Figure 2:
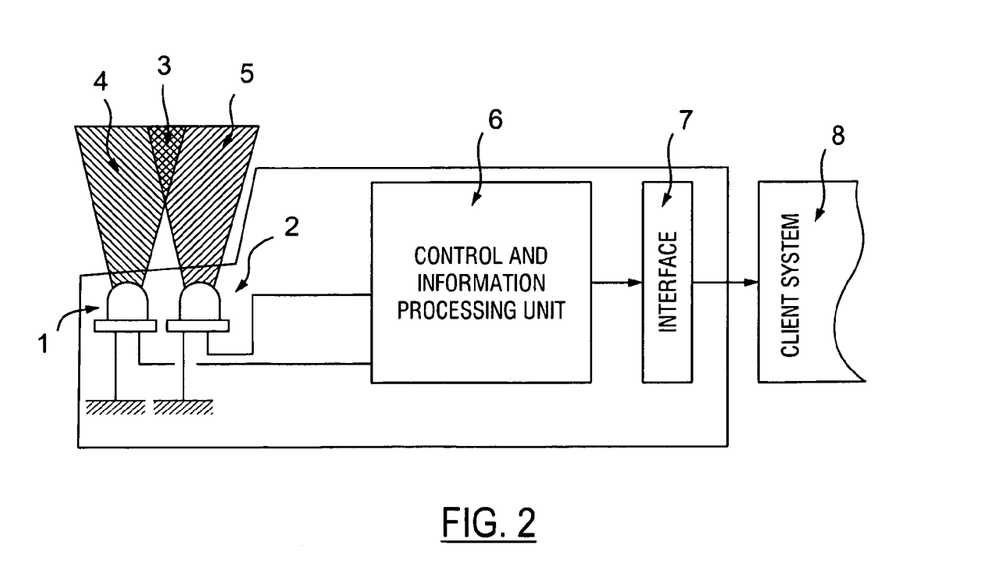
FIG. 2 illustrates a synoptic of the device for detecting gas bubbles in a liquid according to a second arrangement of the light source and the light detector.
Figure 3:
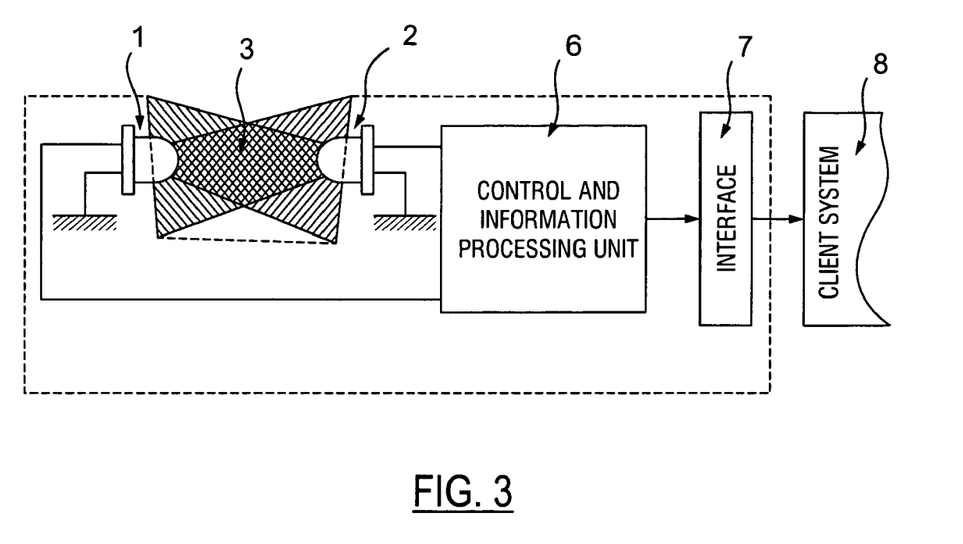
FIG. 3 illustrates a synoptic of the device for detecting gas bubbles in a liquid according to a third arrangement of the light source and the light detector.

FIGS. 1, 2 and 3 illustrate a device according to the present invention comprising essentially a light source 1 and a light detector 2 linked to a control and information processing unit 6.

The interfacing of the device with a client system 8 is carried out via an interface module 7.

As evident from FIGS. 1, 2 and 3, the light is emitted by the light source 1 in an illumination zone 4. The field of vision of the light detector 2 defines a vision zone 5. And the intersection of the vision zone 5 with the illumination zone 4 defines a zone for detection of bubbles 3.

The light source 1 can be any type of source, coherent or not, of electromagnetic radiation (for example a bright lamp, a light-emitting diode, etc.). The light detector 2 is any one of conventional light detectors (for example photodiode, phototransistor, photoresistance, etc.).

The light detector 2 generates an electric signal 17 in response to a quantity of light originating from the light source 1 and perceived by the detector 2 in the vision zone 5. This electric signal 17 is then sent to the data controlling and processing unit 6 so that an associated time variation can be measured.

Several arrangements of the light source 1 and detector 2 can be advantageously selected.

The reflection properties of light on the surface of a gas bubble can be utilised within the scope of the invention. FIGS. 1 and 2 illustrate this instance. When no gas bubble is present in the detection zone 3, the light emitted by the light source 1 is perceived only weakly by the light detector 2. However, when a gas bubble enters the detection zone 3, the incident light emitted by the light source 1 is reflected on the surface of said gas bubble. The reflected light sent by the surface of said bubble is then captured by the light detector 2. The reflected light thus creates a variation in the electric signal 17 on the terminals of the light detector 2.

The light source 1 and the light detector 2 can be arranged orthogonally as illustrated in FIG. 1. The light detector 2 then captures the reflected light in a direction substantially perpendicular to the direction of incidence of the light emitted by the light source 1.

The light source 1 and the light detector 2 can likewise be arranged parallel as illustrated in FIG. 2. The light detector 2 then captures the reflected light in a direction noticeably parallel to the direction of incidence of the light emitted by the light source 1.

The transmission properties of light in environments (liquid, gas) with different optical characteristics can also be used advantageously.

In this instance and as can be seen in FIG. 3, the light source 1 and the light detector 2 are arranged opposite each other such that the light emitted by the source 1 directly strikes the detector 2. The illumination zones 4 and vision zones 5 are noticeably combined and the detection zone 3 corresponds to the trajectory borrowed by the light between its emission by the light source 1 and its reception by the light detector 2.

Different techniques can be selected and especially those relying on the absorption of a specific wavelength or on the diffraction of light rays.

In particular, a light of a specific wavelength strongly absorbed by one of the environments (liquid or gas) and weakly absorbed by the other environment can be employed. The wavelength of the light emitted by the light source 1 in the direction of the light detector 2 can thus be strongly absorbed by the liquid and weakly absorbed by the gas constituting the bubbles.

When no gas bubble is present in the detection zone 3, the light emitted by the light source 1 travels through its path in a liquid with strong absorption coefficient so well that said light is perceived only weakly by the light detector 2. However, when a gas bubble enters the detection zone 3, the light emitted by the light source 1 travels through one part of its path in a gas with a low absorption coefficient. The quantity of light perceived by the light detector 2 when a bubble is present in the detection zone 3 is then more significant than that perceived by the detector when no bubble is present in the detection zone 3. It follows that the passage of a gas bubble into the detection zone 3 creates a variation in the electric signal on the terminals of the light detector 2.

The differences in refraction index which exist between the liquid and the gas constituting the bubbles can also be utilised advantageously.

The light rays emitted by the light source 1 in the direction of the light detector 2 can be deviated when a gas bubble is present in the detection zone 5 due to the differences in refraction index which exist between the liquid and the gas at the level of the surface of the bubbles. The passage of a gas bubble into the detection zone then causes a variation in light intensity perceived by the detector 2, the luminosity at the level of the detector being modified due to the deviation in light rays.

Moreover, the devices according to FIGS. 1 and 2 for which the reflection properties of the light on the surface of a gas bubble are employed work only with respect to variations in the electric signal 17 generated by the light detector 2. If the sensor constituted by the light source 1 and the light detector 2 is no longer immersed in the liquid, no variation in the electric signal 17 is in fact detected. A device for measuring resistivity of the ambient conditions utilising a system of electrodes capable of determining whether the electrodes are immersed in a liquid or in air can advantageously be added to the devices illustrated by FIGS. 1 and 2. Such a device is described in European patent application EP 1 231 463 which can be used as a reference for more information. The incorporation of such a system of electrodes makes it possible to obtain a device capable of determining whether the sensor is immersed in liquid or not.

When a device according to FIG. 3 employs the absorption properties of a specific wavelength as has been described previously, no variation in the electric signal 0.17 generated by the light detector 2 can be detected when the sensor constituted by the source 1 and the light detector 2 is not immersed in the liquid. However, in this case, the quantity of light perceived by the light detector 2 is abnormally high, since the light travels through its entire path in a gas with a low absorption coefficient. This abnormally high value can then be taken into account to determine whether the sensor is immersed in liquid or not.

Similarly, when a device according to FIG. 3 employs the diffraction properties of light rays as has been described previously, no variation in the electric signal 17 generated by the light detector 2 can be detected when the sensor consisting of the source 1 and the light detector 2 is not immersed in liquid. However, the optical materials utilised can be determined for transmitting maximum light when the sensor is in a gas and a much lower quantity when the sensor is immersed in a liquid. The light rays are effectively bent significantly and consequently strongly attracted to the light detector 2 when the light travels through its entire path in a gas. The light rays are on the other hand slightly bent and consequently weakly attracted to the light detector 2 when the light travels its entire path in liquid. The abnormally high quantity of light perceived by the light detector 2 when the sensor is immersed in an ambient conditions constituted by gas to determine whether said sensor is immersed in liquid or not can then be taken into account.

We will now describe the operation of the data controlling and processing unit 6. This is illustrated by FIGS. 4 and 5, which illustrate respectively the first and the second preferred embodiment of the invention.

Figure 4:
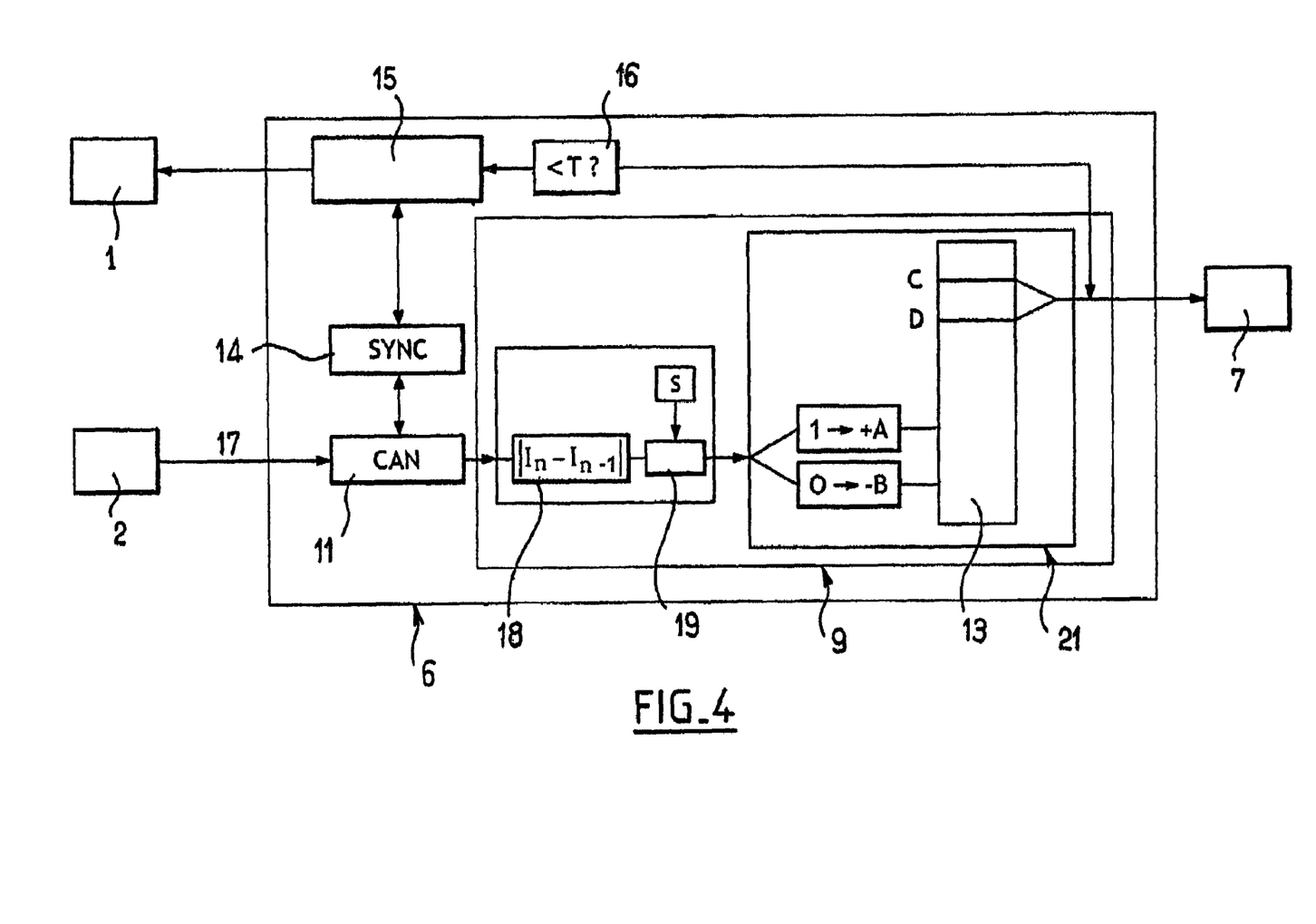
FIG. 4 illustrates a synoptic of an electronic control and processing unit for information according to a first preferred embodiment of the invention.
Figure 5:
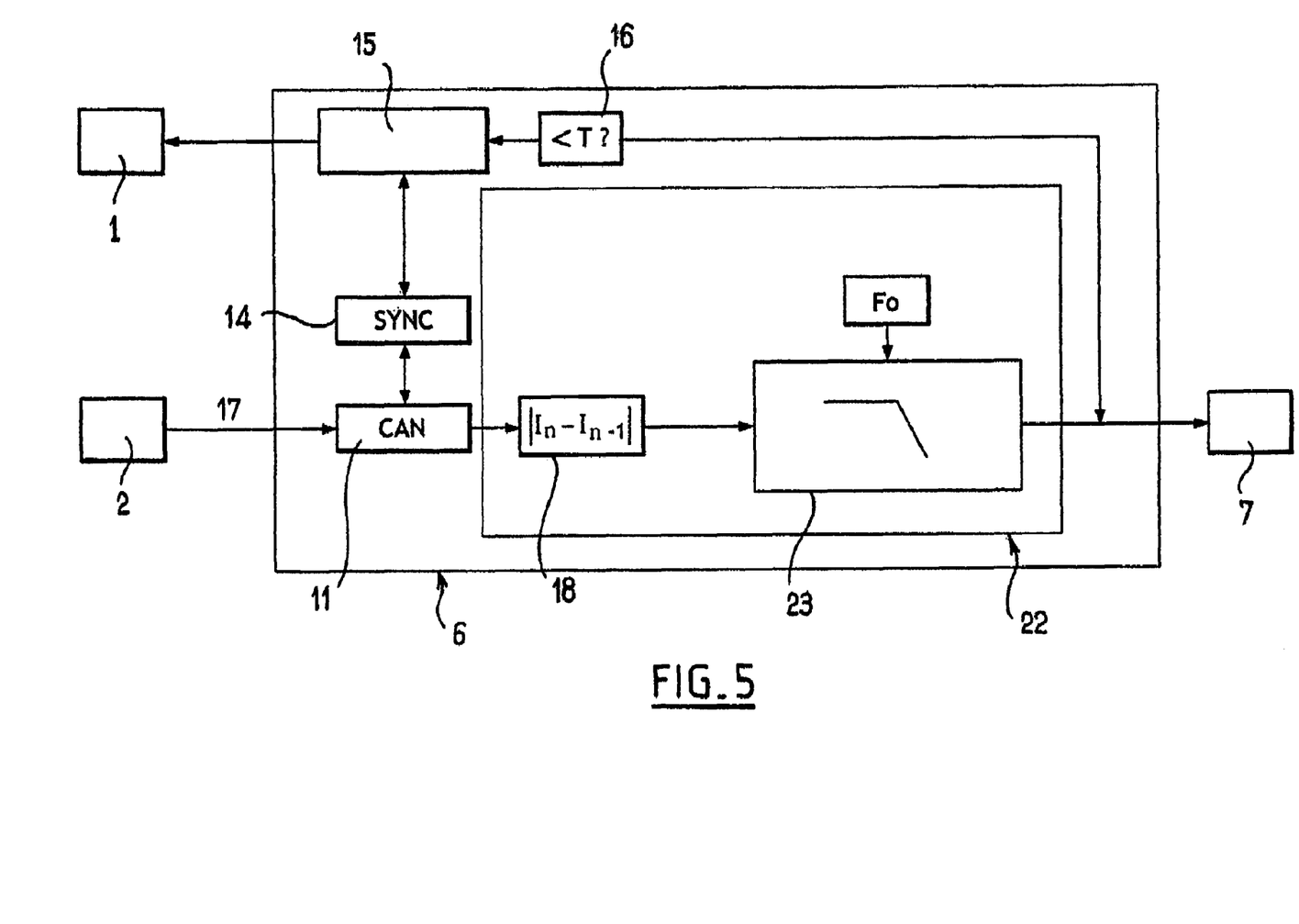
FIG. 5 illustrates a synoptic of an electronic control and processing unit for information according to a second preferred embodiment of the invention.

As is evident from FIGS. 4 and 5, the data controlling and processing unit 6 essentially comprises a control module 15 of the light source 1, an analog/digital conversion module 11 capable of digitising the electric signal 17 generated by the light detector 2 and a module for processing the light intensity in the detection zone of the bubbles 3.

The electric signal 17 generated by the light detector 2 in response to the quantity of light it perceives is digitised via the analog/digital conversion module 11.

The control of the light source 1 must be active during the acquisition of the corresponding signal of the light intensity perceived by the light detector 2. The control of the source is carried out by the control module 15 of the light source and is either continuous or, as is the case within the scope of the description, pulsed and synchronised with the acquisition via a synchronisation module 14.

The control module 15 of the light source is capable of polarising the light source 1 periodically and of measuring the electric signal 17 collected on the light detector 2. The polarisation can be performed on several levels for optimum regulation of the intensity of the light emitted. This calibration is carried out typically by successively testing the possible polarisation values of the light source and by retaining the polarisation value having given the best voltage of the electric signal 17 collected on the light detector, that is, the best aligned voltage in the possible range of voltage. This calibration is carried out at regular intervals to compensate for the deviations of the optical characteristics of the system (soiling, opacification, etc.) as well as those due to variations in temperature. The time interval is typically between 10 s and 1 min. It thus appears that an advantage of the invention lies in the fact that the deviations of the system do not affect the sensitivity of the device used by the invention.

As mentioned previously, the detection of the presence of a gas bubble in the detection zone 3 is carried out by measuring the variation in light intensity perceived by the light detector 2. The time scale for measuring these variations must correspond to the average time taken by a bubble to travel through the detection zone 3, which depends on the size of the detection zone and the velocity of the bubbles to be detected. Typically, the time constant is between a few hundred microseconds and a few milliseconds for a velocity of a few metres per second.

A device for measuring temperature such as that already been described in European patent application EP 1 231 463 to which can be used as a reference for more information can advantageously be added to the device according to the present invention. The incorporation of such a device makes it possible to provide a two-function sensor (temperature of the liquid/presence of gas bubbles in the liquid). As known, a temperature probe which can be short-circuited when the device has detected the presence of bubbles can be utilised.

As seen previously, when the sensor constituted by the light source 1 and the light detector 2 is not immersed in liquid, it is impossible to detect the absence of liquid by measuring the variation in light intensity. The observation via the control module 15 of the light source of the polarisation value of the light source 1 makes it possible to alert the client system to the problem and to substitute the main alarm system.

As mentioned above, when the sensor is not immersed in the liquid, the environment effectively transmits much more light than under normal circumstances. The polarisation value of the light source consequently takes an abnormally low value. An overshoot detector 16 of a predefined polarisation threshold makes it possible to detect whether the sensor constituted by the source and the light detector is immersed in liquid or not.

The client system 8 is then alerted via the interface module 7 of the total absence of liquid at the level of the sensor when the polarisation value of the light source 1 is lower than a predefined threshold value T and is detected as such by the overshoot detector 16 of a predefined polarisation threshold.

This substitute can however be put to use only within the scope of capture technologies by transmission (especially absorption of a specific wavelength and diffraction of light rays on the surface of a bubble) described previously and illustrated by FIG. 3.

Within the scope of capture technologies by reflection described previously and illustrated by FIGS. 1 and 2, analysis of the variations between two successive measurements of the light intensity perceived by the light detector 2 cannot detect whether the sensor is immersed in the liquid or not. In order to make this detection feasible, it is possible to add to the device a system of electrodes as has been described previously. In this way the principal alarm system can be substituted from when the sensor is no longer immersed in the liquid.

According to a first preferred embodiment of the invention, the processing module 9 for light intensity comprises logical comparison means 12 capable of detecting any notable variation in light intensity between two successive measurements, as well as statistical processing means 21 of said variation capable of providing information on whether or not the limited bubble content has been exceeded.

Said logical comparison module 12 is constituted by means 18 capable of calculating the variation in light intensity between two successive measurements made at the level of the light detector 2 and means 19 capable of detecting whether a predetermined threshold S has been exceeded.

In the absence of bubbles, the successive measurements of light intensity are identical. The passage of a bubble in the detection zone 3 modifies the light intensity perceived by the detector 2. This modification of light intensity in the detection zone 3 is conveyed by a variation in the electric signal 17 on the terminals of the light detector 2. It is these time variations which are detected.

The variation in light intensity is then calculated by comparing, via means 18, the value of the electric signal 17 to that previously obtained. The measurement of variation in light intensity between two successive measurements is then compared to a predetermined threshold S via the means 19 for detecting a threshold exceeding. If the difference between these two successive values is greater than the threshold S, the system considers that a bubble is present in the detection zone 3.

In the event of the threshold S being exceeded, the warning counter 13 of the statistical processing means 21 of the variation between successive measurements of light intensity is incremented by a predetermined value A. Otherwise, this same counter is decremented by a value B. The values A and B are such that A is greater than B and their A/B ratio is generally between 10 and 1000.

The warning counter 13 is delimited between two predefined values. If it goes beyond an alarm value C, the data controlling and processing unit 6 would then inform the client system 8 via the interface module 7 that the bubble content is greater than the authorised limited content. Said value C is generally between 70% and 95% of the maximum value of the warning counter 13.

To optimise the system, an hysteresis can be set up by means of a final alarm value D which avoids the transitory problems between the two output states.

The values C and D are fixed such that C is greater than D. According to the cases, the A/C ratio is typically between 1/25 and 1/250 and the D/C ratio typically between 3/10 and 8/10.

A time delay can likewise be added to the system to advantageously increase the functional enhancement of the detector. The choice can be made for example to trigger the alarm only if the warning counter 13 exceeds the alarm value C' over a period greater than the time delay value. The value C' is generally, though not compulsorily, equal to C.

One of the advantages of data processing carried out within the scope of this first preferred embodiment of the invention lies in the fact that the response time is inversely proportional to the quantity of bubbles present in the detection zone. A highly significant presence of bubbles is detected very rapidly, whereas a small quantity is analysed longer and more precisely in order to ensure that the detection is founded. Any false alarm is thus avoided.

According to a second preferred embodiment of the invention, the processing module 22 of light intensity comprises means 18 capable of calculating the variation in light intensity between two successive measurements as well as means 23 capable of extracting the average value from a plurality of said variations between two successive measurements of light intensity.

The variation in light intensity is calculated by comparing, via the means 18, the value of the electric signal 17 previously digitised by the analog/digital conversion module 11 to the value previously acquired. The measurement of the variation in light intensity between two successive measurements is then introduced into a low-pass numerical filter characterised by its coefficients Fo and constituting means 23 capable of extracting the average value from the variations between two successive measurements of light intensity.

The data controlling and processing unit 6 then sends the client system 8, via the interface module 7, this average value which is representative of the bubble content in the liquid.

This second preferred embodiment of the invention makes it possible to indicate reactively the quantity of bubbles present in the liquid. It thus offers a flexibility of use to the client who can regulate or re-regulate the system when desired, even elaborate new alarm strategies, by utilising pre-alarm levels for example.

As seen previously, a temperature measuring device can advantageously be added to the device according to the present invention. A temperature probe which can be short-circuited when the sensor has detected the presence of bubbles and/or when the sensor is not immersed in the liquid can be utilised.

The incorporation of such a temperature measuring device makes it possible to provide a three-function sensor (temperature of liquid/presence of gas bubbles in the liquid/absence of liquid) when capture techniques based on the transmission properties of light in environment having different optical characteristics are employed.

The incorporation of such a temperature measuring device makes it possible to provide a two-function sensor (temperature of liquid/presence of gas bubbles in the liquid) when capture techniques based on the reflective properties of light on the surface of gas bubbles are employed. If, as has been seen previously, a system of electrodes is furthermore incorporated, the third functionality (absence of liquid) is advantageously added to the device according to the invention.

Figure 6:
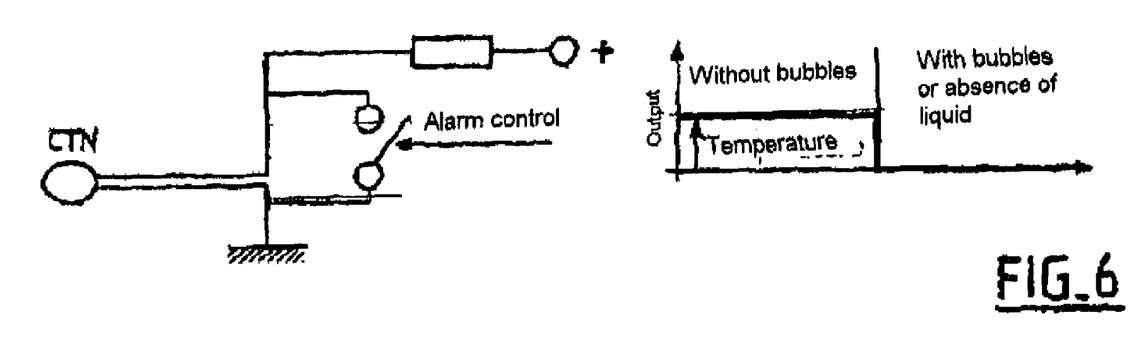
FIG. 6 illustrates the interfacing of the electronic data controlling and processing unit with a client system within the scope of the first preferred embodiment of the invention.
Figure 7:
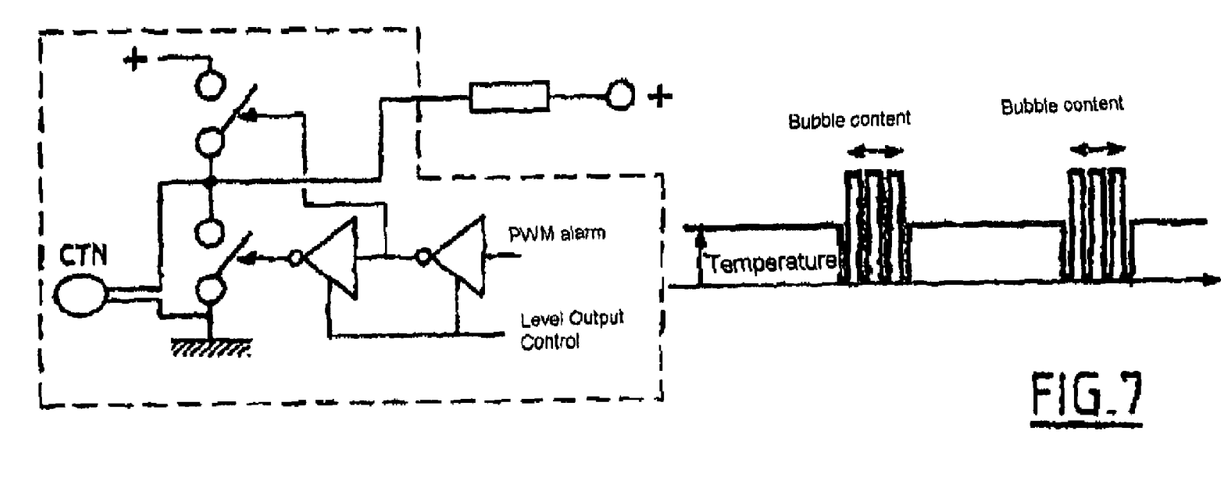
FIG. 7 illustrates the interfacing of the electronic data controlling and processing unit with a client system within the scope of the second preferred embodiment of the invention.

The interfacing with the client system 8 can advantageously be carried out, as is illustrated by FIGS. 6 and 7, by utilising only a single connection wire simultaneously carrying information concerning the temperature of the liquid, the presence of bubbles in the liquid and, according to certain configurations, the absence of liquid.

FIG. 6 illustrates such interfacing within the scope of the first preferred embodiment of the invention. When the sensor has detected the presence of bubbles or the absence of liquid, an alarm signal is generated. This alarm signal controls the short-circuiting of the temperature probe. In such a way, the outgoing signal for the client system 8 is at a high-amplitude level proportional to the temperature of the liquid when the sensor is immersed in the liquid and when no bubble is detected in the detection zone. Said signal takes a low level following short-circuiting of the probe when the sensor has detected the presence of bubbles or the absence of liquid.

The FIG. 7 illustrates the interfacing which can be carried out within the scope of the second preferred embodiment of the invention. At regular intervals information on the bubble content is sent in the form of a train of PWM strobes (Pulse Width Modulation or in French Modulation de Duree et d'Impulsion). For this, the value of the voltage of the variable resistance forming the temperature measuring device is periodically pre-set to the ground and feeder voltage of the sensor. The width of the pulses is proportional to the measured bubble content. An absence of liquid at the level of the sensor is considered as a maximum bubble content and is thus illustrated by a train of pulses of maximum width. The output signal for the client system 8 is thus constituted by the periodic succession of a constant high-amplitude signal level proportional to the temperature of the liquid and a PWM signal representative of the bubble content in the liquid.

As indicated previously, the invention applies in particular, though not exclusively, to the detection of gas bubbles in a cooling circuit of an internal combustion engine of a motor vehicle.

For this purpose, it is noted that the parameters A, B, C, C', D, S, T, the coefficients of the filter (Fo), as well as the frequency at which acquisitions are made can be regulated according to the characteristics of the system to be monitored. Action can thus be taken especially on the response time, the sensitivity in accordance with the velocity of the bubbles, etc.

Of course, the invention is not limited to the particular embodiments which have just been described, but extends to any variant in keeping with its spirit.

The invention claimed is:

1. A process for detection of gas bubbles in a liquid in a water circuit for cooling an internal combustion engine adapted to a device comprising: a light source, a light detector, wherein the light source and the light detector are immersed in the liquid in the water circuit cooling the internal combustion engine, and a data controlling and processing unit linked to a client system, comprising the steps of:

emitting light from the light source for acquisition of a first measurement and a subsequent measurement known as a successive measurement of light intensity perceived by the light detector, and for calculation of a variation between two successive measurements of said light intensity;

incrementing a warning counter by a predefined value A when the variation in light intensity perceived by the light detector between two successive measurements is greater than the threshold S and decrementing said warning counter by a predefined value B in the opposite case; and sending to the client system information indicating that the bubble content is greater than an authorized maximum content when said warning counter exceeds a predefined alarm value C over a period greater than a predefined time delay period.

2. A process for detection of gas bubbles in a liquid in a water circuit for cooling an internal combustion engine adapted to a device comprising: a light source, a light detector, wherein the light source and the light detector are immersed in the liquid in the water circuit cooling the internal combustion engine, and a data controlling and processing unit linked to a client system, comprising:

emitting light from the light source for acquisition of a first measurement and a subsequent measurement known as a successive measurement of light intensity perceived by the light detector, and for calculation of a variation between two successive measurements of said light intensity;

comparing the variation between the two successive measurements to a predefined threshold value S;

incrementing a warning counter by a predefined value A when the variation in light intensity perceived by the light detector between two successive measurements is greater than the threshold S;

decrementing said warning counter by a predefined value B in the opposite case;

sending to the client system information indicating that a bubble content is greater than an authorized maximum content when said warning counter exceeds a predefined alarm value C, wherein the process further comprises a ceasing step of sending to the client system information indicating that the bubble content is greater than the authorized maximum content when the warning counter is less than a predefined final alarm value D.

3. The process according to claim 2, further comprising calculating an average value from a plurality of variations between two successive measurements of light intensity.

4. The process according to claim 3, further comprising sending to the client system information indicating the average value of the successive variations of the light intensity perceived by the light detector.

5. The process according to claim 2, wherein the light source and the light detector are arranged noticeably orthogonally, acquiring successive measurements of the intensity of light reflected from the surface of a gas bubble in a direction noticeably orthogonal to the direction of incidence towards the light detector.

6. The process according to claim 2, wherein the source and the light detector are arranged noticeably adjacently, acquiring successive measurements of the intensity of light reflected from the surface of a gas bubble in a direction noticeably parallel to the direction of incidence towards the light detector.

7. The process according to claim 5, further comprising a temperature measuring element and at least one switch linked to said temperature measuring element, wherein the switch is configured to change state during the detection of a gas bubble.

8. The process according to claim 7, wherein the data controlling and processing unit transmits a high-amplitude level signal proportional to the temperature of the liquid when the presence of a bubble is not detected or low level when the presence of a bubble is detected, via an interface module to the client system, and wherein the interface module and the client system are linked only by a single wire.

9. The process according to claim 2, wherein the source and the light detector are arranged noticeably opposite each other, making it possible to send out a light of a specific wavelength from the light source such that it is strongly (reciprocally weakly) absorbed by the liquid and slightly (reciprocally strongly) absorbed by the gas constituting the bubbles.

10. The process according to claim 2, wherein the source and the light detector are arranged noticeably opposite each other, acquiring successive measurements of light intensity deflected towards the light detector should the case arise in the presence of bubbles due to the diffraction index differences between the liquid and the gas constituting the bubbles at the level of the surface of said bubbles.

11. The process according to claim 9, further comprising a temperature measuring element and at least one switch linked to said temperature measuring element, wherein the switch is configured to change state periodically.

12. The process according to claim 11, wherein the data controlling and processing unit is linked to the client system via an interface module and transmits, via the interface module, to the client system, information on the temperature of the liquid and the presence of bubbles in the liquid, wherein the interface module and the client system are linked only by a single wire, and wherein a periodic signal is supplied to the client system by the interface module.

13. The process according to claim 12, wherein the period of said periodic signal is formed by a first phase constituted by a constant high-amplitude level signal proportional to the temperature of the liquid and by a second phase constituted by a train of pulses of modulated width, and wherein the width of the impulses is modulated according to the average value of the successive variations in light intensity perceived by the light detector.

14. A process for detection of gas bubbles in a liquid in a water circuit for cooling an internal combustion engine adapted to a device comprising: a light source, a light detector, and a data controlling and processing unit linked to a client system, wherein the light source and the light detector are immersed in the liquid in the water circuit cooling the internal combustion engine, wherein the data controlling and processing unit comprising a control module of the light source is configured to periodically polarize said light source on several polarization levels, comprising the steps of:

emitting light from the light source
for acquisition of a first measurement and a subsequent measurement known as a successive measurement of light intensity perceived by the light detector, and
for calculation of a variation between two successive measurements of said light intensity.

15. The process according to claim 14, wherein calibration of the source and the light detector is carried out synchronously by periodic polarization of the light source.

16. A process for detection of gas bubbles in a liquid in a water circuit for cooling an internal combustion engine adapted to a device comprising: a light source, a light detector, a data controlling and processing unit linked to a client system via an interface module, and a system of electrodes configured to measure the resistivity of the ambient conditions, wherein, the client system is informed, via the interface module, by the data controlling and processing unit, that the source and the light detector are not immersed in the liquid when the system of electrodes identifies the ambient conditions as not being the liquid, comprising the steps of:

emitting light from the light source for acquisition of a first measurement and a subsequent measurement known as a successive measurement of light intensity perceived by the light detector, and for calculation of a variation between two successive measurements of said light intensity.

17. The process according to claim 16, further comprising a temperature measuring element and at least one switch linked to said temperature measuring element, wherein the switch is configured to change state during the detection of a gas bubble and during the absence of liquid.

18. The process according to claim 16, wherein the data controlling and processing unit transmits a high-amplitude level signal proportional to the temperature of the liquid when the presence of a bubble is not detected and when the light source and the light detector are immersed in the liquid, via the interface module to the client system, wherein the data controlling and processing unit transmits a low level signal when the presence of a bubble is detected or when the light source and the light detector are not immersed in the liquid, via the interface module to the client system, and wherein the interface module and the client system are linked only by a single wire.

19. A process for detection of gas bubbles in a liquid in a water circuit for cooling an internal combustion engine adapted to a device comprising:

a light source, and a light detector and a data controlling and processing unit linked to a client system via an interface module, wherein the source and the light detector are arranged noticeably opposite each other, making it possible to send out a light of a specific wavelength from the light source such that it is strongly (reciprocally weakly) absorbed by the liquid and slightly (reciprocally strongly) absorbed by the gas constituting the bubbles, and wherein the client system is informed, via the interface module, that the sensor is not immersed in liquid when the polarization value of the light source is lower than a predefined threshold value T, known as the polarization alarm threshold value, comprising the steps of:

emitting light from the light source for acquisition of a first measurement and a subsequent measurement known as a successive measurement of light intensity perceived by the light detector, and for calculation of a variation between two successive measurements of said light intensity.

20. The process according to claim 19, further comprising a temperature measuring element and at least one switch linked to said temperature measuring element, wherein the switch is configured to change state periodically.

21. The process according to claim 20, wherein the data controlling and processing unit transmits, via the interface module, to the client system the information on the temperature of the liquid, the presence of bubbles in the liquid and the non-immersion of the sensor in the liquid, wherein the interface module and the client system being linked only by a single wire, and wherein a periodic signal is supplied to the client system by the interface module.

22. The process according to claim 21, wherein the period of said periodic signal is formed from a first phase constituted by a constant high-amplitude level signal proportional to the temperature of the liquid and a second phase constituted by a train of pulses of modulated width, and wherein the width of the impulses is modulated according to the average value of the successive variations in light intensity perceived by the light detector and said width becomes maximum when the sensor is not immersed in the liquid.

* * * * *